United States Patent [19]

Knauf et al.

[11] Patent Number: 4,857,510
[45] Date of Patent: Aug. 15, 1989

[54] COMPOSITIONS FOR COMBATING PESTS CONTAINING MACROCYCLIC LACTONES

[75] Inventors: Werner Knauf, Eppstein; Anna Waltersdorfer, Frankfurt am Main; Alfons Sagenmüller, Kelsterbach; Hubert Stier, Flörsheim am Main, all of Fed. Rep. of Germany; Jan Lourens, Makati, Philippines

[73] Assignee: Hoechst Aktiengesellschaft, Frankfurt am Main, Fed. Rep. of Germany

[21] Appl. No.: 6,569

[22] Filed: Jan. 23, 1987

[30] Foreign Application Priority Data

Jan. 25, 1986 [DE] Fed. Rep. of Germany ....... 3602276
Sep. 17, 1986 [DE] Fed. Rep. of Germany ....... 3631559

[51] Int. Cl.[4] .............................................. A61K 31/70
[52] U.S. Cl. ..................................................... 514/30
[58] Field of Search ......................................... 514/30

[56] References Cited

FOREIGN PATENT DOCUMENTS 842565 4/1984 South Africa .
842567 4/1984 South Africa .

OTHER PUBLICATIONS

*The Pesticide Manual*, 7th Edition, pp. 190 and 247.

*Primary Examiner*—Johnnie R. Brown
*Assistant Examiner*—Elli Peselev
*Attorney, Agent, or Firm*—Curtis, Morris & Safford

[57] ABSTRACT

Combinations of compounds of the formula I

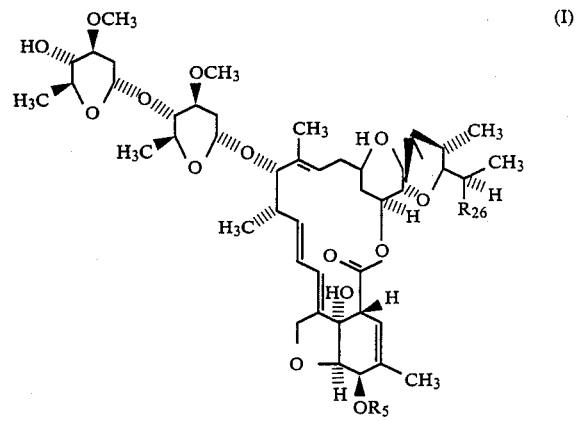

in which $R_5$ denotes H or $CH_3$; $R_{26}$ denotes $CH_3$ or $C_2H_5$;

and X denotes $-CH=CH-$, $-CH_2-\overset{OH}{\underset{}{CH}}-$ or $-CH_2-CH_2$, with a selected insecticide from the group comprising phosphoric acid esters, carbamates and carboxylic acid esters, or an insecticide of the formula II

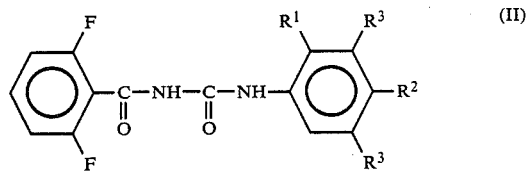

in which $R^1$ denotes H or F, $R^2$ denotes F, halogenoalkoxy, (substituted) phenoxy or (substituted) pyridyloxy and $R^3$ denotes H or Cl, or an active compound from the group comprising azocyclotin, binapacryl, bensultap, bisclofentezin, buprofecin, cartap, cyromacin, endosulfan, ethoproxyfen, fenoxycarb, flubenzimin, hexythiazox, ethofenprox, 5-[4-(4-ethoxyphenyl)-4-methylpentyl]-2-fluoro-1,3-diphenyl ether, 3-(2-chlorophenyl)-3-hydroxy-2-(2-phenyl-4-thiazolyl)-propenenitrile and thiocyclam, with *Bacillus thuringiensis* or a nuclear-polyhedral or granulosis virus have surprising advantageous actions when used against harmful insects and acarides.

1 Claim, No Drawings

COMPOSITIONS FOR COMBATING PESTS CONTAINING MACROCYCLIC LACTONES

Some compounds which have an insecticidal and acaricidal action are known from the group of microbial metabolites. These compounds include those of the class of avermectins and derivatives thereof. These compounds are a substance mixture of macrocyclic lactones of the formula I

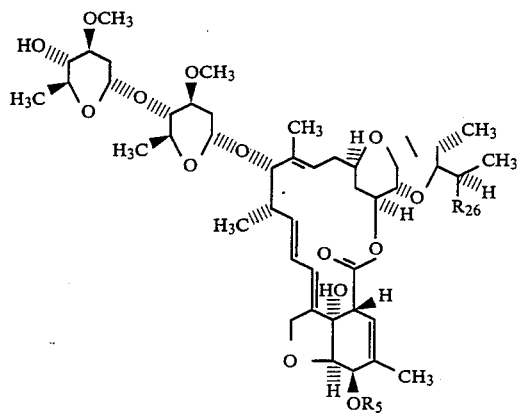

in which the substituents may have the following meanings:

$R_5 = H$ or $CH_3$
$R_{26} = CH_3$ or $CH_2H_5$ and

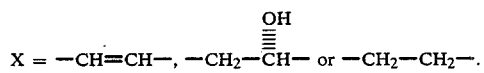

$X = -CH=CH-, -CH_2-CH- $ or $-CH_2-CH_2-$.

These are isolated from the microorganism *Streptomyces avermitilis*, see Fisher, M. H.: The Avermectins in Recent Advances in the Chemistry of Insect Control edited by N. F. Janes; 1985; the mixture essentially consists of eight components, components $A_{1a}$, $A_{1b}$, $A_{2a}$, $A_{2b}$, $B_{1a}$, $B_{1b}$, $B_{2a}$ and $B_{2b}$, see I. Putter et al., Experientia 37 (1981) page 963, Birkhäuser Verlag (Switzerland). In addition, synthetic derivatives, in particular dihydro derivatives ($X = -CH_2-CH_2$) are also of interest, for example the product ivermectin, see Dybas, Green, British Crop Protection Conference, Pests and Diseases, pages 947 and 951 (1984).

Combinations of avermectins and certain insecticides are furthermore described in South African Patent Applications No. 842,565 and No. 842,567.

Novel combinations of avermectins and derivatives of the formula I with other selected insecticides and acaricides have now been found, in which, surprisingly, synergistic actions arise.

The invention therefore relates to agents for combating pests, which contain at least one compound of the formula I in combination with a phosphoric acid ester from the group comprising azinphos-ethyl, azinphosmethyl, 1-(4-chlorophenyl)-4-[(O-ethyl, S-propyl)phosphoryloxy]pyrazole (TIA-230), coumaphos, demeton, demeton-S-methyl, dimethoate, ethoprophos, etrimfos, fenitrothion, fenthion, heptenophos, phosalon, pirimophos-ethyl, pirimophos-methyl, profenofos, prothiofos, sulprofos and triazophos, or a carbamate from the group comprising bendiocarb, BPMC (2-(1-methylpropyl)phenyl methylcarbamate), butocarboxime, butoxycarboxime, carbosulfan, cloethocarb, isoprocarb, oxamyl, pirimicarb, promecarb and thiodicarb, or a carboxylic acid ester from the group comprising allethrin, alphametrin, bioallethrin, bioresmethrin, cycloprothrin, cyfluthrin, cyhalothrin, α-cyano-3-phenyl-2-methyl-benzyl 2,2-dimethyl-3-(2-chloro-2-trifluoromethylvinyl)cyclopropanecarboxylate (FMC 54800), fenpropathrin, fenfluthrin, flucythrinate, flumethrin and tralomethrin, or a benzoylurea of the formula II

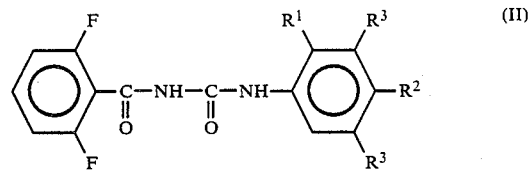

in which $R^1$ denotes H or F, $R^2$ denotes fluorine, $(C_1-C_4)$halogenoalkoxy, phenoxy or pyridyloxy, both of which are substituted by one to three radicals from the group comprising chlorine and trifluoromethyl and $R^3$ denotes H or Cl, or an active compound from the group comprising azocyclotin, binapacryl, bensultap, bisclofentezin, buprofectin, cartap, cyromacin, endosulfan, ethoproxyfen, fenoxycarb, flubenzimin, hexythiazox, ethofenprox (MTI-500), 5-[4-(4-ethoxyphenyl)-4-methylpentyl]-2-fluoro-1,3-diphenyl ether (MTI 800), 3-(2-chlorophenyl)-3-hydroxy-2-(2-phenyl-4-thiazolyl)-propenenitrile (SN 72129) and thiocyclam, with *Bacillus thuringiensis* or a nuclear-polyhedral or granulosis virus, such as *Cydia pomonella* granulosis virus (CpGV).

The avermectins of the formula I are as a rule employed as mixtures. The product abamectin, which essentially contains the $B_1$ avermectins, is of particular interest here, see K. E. Nowels, Agrichem. Age., January 1985, page 28.

$(C_1-C_4)$Halogenoalkoxy in formula II contains, in particular, one or more fluorine or chlorine atoms. The tetrafluoroethoxy radical is of particular importance.

The following compounds IIa–IId are examples of compounds of the formula II:

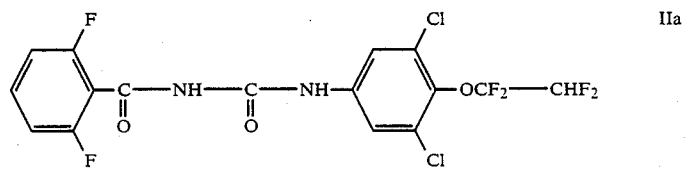

IIa

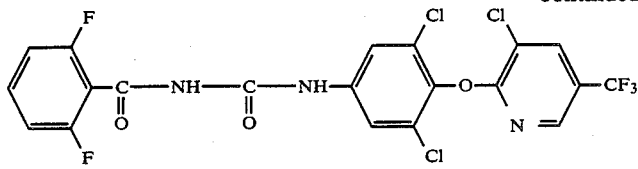

IIb

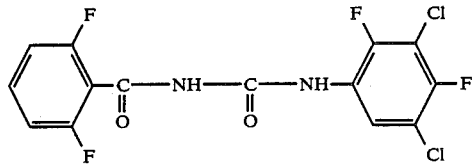

IIc

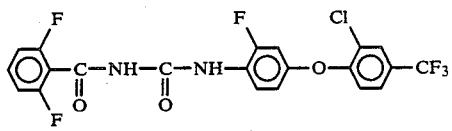

IId

The abovementioned active compounds for which common names have been given are, with the few exceptions mentioned below, described in CH. R. Worthing, S. B. Walker, the Pesticide Manual, 7th edition British Crop Protection Council (1983).

The other compounds are described in the following publications:

TIA-230:
IUPAC Congress report, Pesticide Chemistry 1982, Kyoto Japan.

FMC 54800:
H. J. Doel et al., FMC 54800, A New Acaricide-Insecticide, Symposium Gent (1984)

MTI 500, MTI 800:
Recent Advances in the Chemistry of Insect Control, Int. Symposium 25-27 September 1984, Cambridge SN 72129:
E. P. Pieters et al., Field Expierience with SN 72129, A New Selective Insecticide, 17th Int. Congress of Entomology 1984, Hamburg.

Compound IIa has been disclosed under the code name XRD-473, see Sbragia, R. J. et al, Proceeding 10th Int. Congress Plant Protection (1983), Brighton, Volume 1, pages 417-424. Compound IIb has the common name chlorfluazuron (Neumann, R. and Guyer, W. Proc. loc. cit. pages 445-451), compound IIc has the common name teflubenzuron (Becher, H. M. et al., Proc. loc. cit. 408-415) and compound IId has the common name flufenoxuron (Anderson, H. et al., Proceedings Volume 1, pages 89-96, British Crop Prot. Conf. (1986)).

Of the combination partners for the compounds of the formula I, the active compounds which are of particular interest according to the invention are binapacryl, endosulfan, heptenophos, hexythiazox, triazophos and the compounds of the formulae IIa to IId, and of the latter in particular IIc (teflubenzuron).

According to the invention, the compounds of the formula I can also be combined with two or more of the active compounds listed.

The insecticidal and acaricidal activity of the active compound combinations according to the invention is considerably more potent than was to be expected from the actions of the individual components. By using these combinations, the amounts of the individual components applied can therefore be reduced. Their use accordingly provides economic and ecological advantages.

The agents according to the invention have a good plant tolerance and favorable toxicity toward warm blooded animals and are suitable for combating animal pests, in particular insects, arachnids and nematodes, particularly preferably for combating insects, and their development stages, which occur in agriculture, in forests, in the protection of stored products and materials and from the hygiene sector. They are active against normally sensitive and resistant types and against all or individual development stages. The abovementioned pests include:

From the order of the Isopoda, for example *Oniscus asellus, Armadillidium vulgare* and *Porcellio scaber.* From the order of the Diplopoda, for example *Blaniulus guttulatus.* From the order of the Chilopoda, for example *Geophilus carpophagus* and *Scutigera* spp. From the order of the Symphyla, for example *Scutigerella immaculata.* From the order of the Thysanura, for example *Lepisma saccharina.* From the order of the Collembola, for example *Onychiurus armatus. From the order of the Orthoptera, for example Blatta orientalis, Periplaneta americana, Leucophaea maderae, Blatella germanica, Acheta domesticus,* Gryllotalpa spp., *Locusta migratoria migratorioides, Melanoplus differentialis* and *Schistocerca gregaria.* From the order of the Dermaptera, for example *Forficula auricularia.* From the order of the Isoptera, for example *Reticulitermes* spp. From the order of the Anoplura, for example *Phylloera vastatrix,* Pemphigus spp., *Pediculus humanus corporis,* Haematopinus spp. and Linognathus spp. From the order of the Mallophaga, for example Trichodectes spp. and Damalinea spp. From the order of the Thysanoptera, for example *Hercinothrips femoralis* and *Thrips tabaci.* From the order of the Heteroptera, for example Eurygaster spp., *Dysdercus intermedius, Piesma quadratum, Cimex lectularius, Rhodnius prolixus* and Triatoma spp. From the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma Lanigerum, Hyalopterus arundinis, Macrosiphum avenae,* Myzus spp., *Phorodon humuli, Rhopalosiphum padi,* Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example *Pectinophora gossypiella, Bupalus piniarius, Cheimatobia brumata, Lithocolletis blancardella,*

*Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilialis, Ephestia kuehniella, Galleria mellonella, Cacoecia podana, Capua reticulana, Choristoneura fumiferana, Clysia ambiguella, Homona magnanima* and *Tortrix viridana.* From the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example Diprion spp., Hoplocampa spp. Lasius spp., *Monomorium pharaonis* and Vespa spp. From the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example *Xenopsylla cheopis* and Ceratophyllus spp. From the order of the Arachnida, for example *Scorpio maurus* and *Latrodectus mactans.*

Combinations of compounds I with compounds of the formula II are particularly suitable for use against pests from the genera Plutella sp., Spodoptera sp., Alabama sp., Anticarsia sp., Pseudoplusia sp., Pieris sp., Scrobipalpua sp., Trichoplusia sp., Choristoneura sp., Lymantria sp., Laspeyresia sp., Psylla sp., Epilachna sp., Leptinotarsa sp., Liriomyza sp., Bemisia sp., Trialeurodes sp., for example in cotton, soya, vegetable, fruit, citrus, wine and maize crops.

It is also possible for various types of spider mites, such as the fruit tree spider mite (*Panonychus ulmi*), the citrus spider mite (*Panonychus citri*) and the common spider mite (*Tetranychus urticae*), including strains resistant to phosphoric acid esters), to be combated well.

The agents according to the invention in general contain the active compounds of the formula I in an amount of 1–95% by weight. They can be used as wettable powders, emulsifiable concentrates, solutions for spraying, dusting agents or granules in the customary formulations.

Wettable powders are preparations which are uniformly dispersable in water and which, in addition to the active compound and as well as a diluent or inert substance, also contain wetting agents, for example polyoxyethylated alkylphenols, polyoxyethylated fatty alcohols and alkyl- or alkylphenol-sulfonates, and dispersing agents, for example sodium lignin-sulfonate, sodium 2,2'-dinaphthylmethane-6,6'-disulfonate, sodium dibutylnaphthalenesulfonate or sodium oleylmethyltauride.

Emulsifiable concentrates are prepared by dissolving the active compound in an organic solvent, for example butanol, cyclohexanone, dimethylformamide, xylene or higher-boiling aromatics or hydrocarbons, with the addition of one or more emulsifiers. Examples of emulsifiers which can be used are: calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylenesorbitan fatty acid esters or polyoxyethylenesorbitol esters.

Dusting agents are obtained by grinding the active compound with finely divided solid substances, for example talc or natural clays, such as kaolin, bentonite, poryphillite or diatomaceous earth. Granules can be prepared either by spraying the active compound onto an adsorbent granular inert material or by applying active compound concentrates to the surface of carriers, such as sand or kaolinites, or of a granular inert material by means of adhesives, for example polyvinyl alcohol, sodium polyacrylate or mineral oils. Suitable active compounds can also be prepared in the manner customary for the preparation of fertilizer granules—if desired as a mixture with fertilizers.

The weight ratio of the compound of the formula I to the combination partner in the agents according to the invention varies in the range from 20:1 to 1:150 depending on the combination partner to be used, for example in particular from 5:1 to 1:5 in the case of the compounds IIa–IId; the use concentrations of the combinations can likewise vary within wide limits, depending on the combination partner to be used, in particular between 0,001 and 1,5 kg/ha and in particular between 0.005 and 0.1 kg/ha in the case of the compounds IIa–IId.

Instead of the avermectins, it is also possible for other microbial metabolites, for example those of the nikkomycin class, such as, for example, nikkomycin Z of the formula

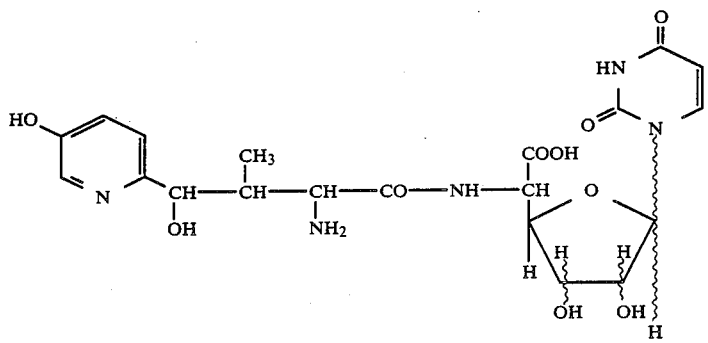

(Wegler: Chemie der Pflanzenschutz- und Schädlingsbekämpfungsmittel (Chemistry of Plant Protection Agents and Agents for Combating Pests), Volume 6, page 265, Springer-Verlag, 1981) or compounds from the milbemycin class, such as, for example, milbemycin $\beta_1$, $\beta_2$ or $\beta_3$ of the formula

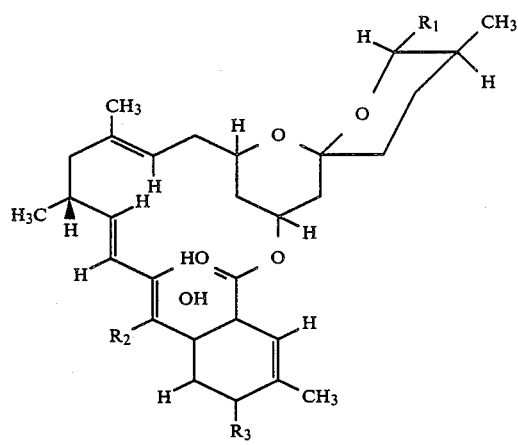

$\beta_1: R_1 = CH_3, R_2 = CH_2OH, R_3 = OCH_3$
$\beta_1: R_1 = C_2H_3, R_2 = CH_2OH, R_3 = OCH_3$
$\beta_1: R_1 = CH_3, R_2 = CH_3, R_3 = OH$ (Wegler: Chemie der Pflanzenschutz- und Schädlingsbekämpfungsmittel (Chemistry of Plant Protection Agents and Agents for Combating Pests), Volume 6, page 305, Springer-Verlag, 1981).

to be advantageously combined with the abovementioned insecticides.

The following examples serve to illustrate the invention.

Biological examples

Tank mixes of the active compounds in suitable formulations were applied in all the examples.

EXAMPLE I

| Test object: | Trialeurodes vaporariorum (eggs) |
| Test plant: | Phaseolus vulgaris |
| Nature of treatment: | Spraying until the formulation starts to drip off |
| Compound | Active compound concentration (ppm) | % mortality after 14 days |
|---|---|---|
| Abamectin (Ia) | 3.9 | 65 |
| | 2.0 | 50 |
| Heptenophos | 125 | 0 |
| | 63 | 0 |
| Ia + heptenophos | 3.9 + 125 | 92 |

-continued

| Test object: | Trialeurodes vaporariorum (eggs) |
| Test plant: | Phaseolus vulgaris |
| Nature of treatment: | Spraying until the formulation starts to drip off |
| Compound | Active compound concentration (ppm) | % mortality after 14 days |
|---|---|---|
| (1:32) | 2.0 + 63 | 80 |

EXAMPLE II

| Test object | Tetranychus urticae |
| Test plant: | Phaseolus vulgaris |
| Nature of treatment: | Spraying until the formulation starts to drip off |

| Compound | Active compound concentration (ppm) | % mortality after 7 days | |
|---|---|---|---|
| | | acaricidal | ovicidal |
| Abamectin (Ia) | 0.49 | 80 | 0 |
| | 0.24 | 45 | 0 |
| | 0.12 | 20 | 0 |
| Binapacryl | 63 | 97 | 75 |
| | 31 | 92 | 50 |
| | 16 | 40 | 25 |
| Ia + binapacryl | 0.49 + 63 | 100 | 100 |
| (1:128.6) | 0.24 + 31 | 97 | 90 |
| | 0.12 + 16 | 90 | 50 |

EXAMPLE III

| Test object: | Prodenia litura (larva stage L3) |
| Test method: | Substrate treatment + animal treatment (dish test) |
| Nature of treatment: | Spraying analogously to 600 l/ha |
| Compound | Active compound concentration (ppm) | % mortality after 7 days |
|---|---|---|
| Abamectin (Ia) | 1000 | 90 |
| | 500 | 30 |
| | 250 | 10 |
| | 125 | 0 |
| Binapacryl | 2000 | 0 |
| | 1000 | 0 |
| Ia + binapacryl | 1000 + 2000 | 100 |
| (1:2) | 500 + 1000 | 90 |
| | 250 + 500 | 70 |
| | 125 + 250 | 10 |

EXAMPLE IV

| Treatment, test object, test plant as for Example II | | |
|---|---|---|
| Compound | Active compound concentration (ppm) | % mortality after 14 days |
| Abamectin (Ia) | 3.9 | 70 |
|  | 2.0 | 60 |
| Endosulfan | 125 | 0 |
|  | 63 | 0 |
| Ia + endosulfan | 3.9 + 125 | 100 |
| (1:32) | 2.0 + 63 | 90 |

EXAMPLE V

| Test object: | | Panonychus ulmi |
|---|---|---|
| Test plant: | | Malus spp. |
| Nature of treatment: | | see Example I |
| Compound | Active compound concentration (ppm) | % mortality after 9 days acaricidal |
| Abamectin (Ia) | 0.49 | 45 |
|  | 0.24 | 30 |
| Hexythiazox | 0.98 | 30 |
|  | 0.49 | 15 |
| Ia + hexythiazox | 0.49 + 0.98 | 100 |
| (1:2) | 0.24 + 0.49 | 70 |

EXAMPLE VI

| Treatment, test object, test plant as for Example II | | | |
|---|---|---|---|
| Compound | Active compound concentration (ppm) | % mortality after 7 days acaricidal | ovicidal |
| Abamectin (Ia) | 0.12 | 80 | 0 |
|  | 0.06 | 30 | 0 |
|  | 0.03 | 15 | 0 |
| Hexythiazox | 0.49 | 10 | 30 |
|  | 0.24 | 0 | 0 |
|  | 0.12 | 0 | 0 |
| Ia + hexythiazox | 0.12 + 0.49 | 100 | 50 |
|  | 0.06 + 0.24 | 70 | 30 |
| (1:4) | 0.03 + 0.12 | 50 | 0 |

EXAMPLE VII

| Test object: | Prodenia litura (larva stage $L_3$) |
|---|---|
| Test method: | Substrate treatment + animal treatment (dish test) |
| Nature of treatment: | Spraying analogously to 600 l/ha |

| Compound | Active compound concentration (ppm) | % mortality after 7 days |
|---|---|---|
| Abamectin (Ia) | 1000 | 90 |
|  | 500 | 30 |
| Hexythiazox | 2000 | 0 |
|  | 1000 | 0 |
| Ia + hexythiazox | 1000 + 2000 | 100 |
| (1:2) | 500 + 1000 | 56 |

EXAMPLE VIII

Vegetables, in this case: head cabbage (*Brassica oleracea*), infested with the diamond-back moth Plutella sp. were treated under open-air conditions with avermectin (I) and teflubenzuron (IIc), in each case by themselves and in combination in the dosages shown below.

On the treated cabbage fields and the untreated control plots, 1, 3 and 6 days after the treatments the average number of diamond-back moths on in each case 10 plants per repetition with a total of 4 repetitions per experiment was determined.

To determine the effectiveness, the values found were computed as follows in accordance with the formula of Abbott (Ab), see S. W. Abbott, J. J. Econ, Entomol. Volume 18 (1925) pages 265–267:

% action (Ab) = untreated minus treated: untreated × 100

The number of plants per 20 square meters was used to determine the weight. The quality was classified in 3 classes (A, B and C), class A being the best quality (cabbage heads without any damage by eating), class B showed slight damage by eating and class C was of poor quality.

| g of active compound/ha | | Insecticidal action Ab in % | | | Absolute yield | % of this in class | | |
|---|---|---|---|---|---|---|---|---|
| Active compound IIc | Abamectin Ia | after 1 | 3 | 6 days | kg/20 m² | A | B | C |
| Individual use | | | | | | | | |
| 1. 7.5 | — | 72 | 66 | 72 | 60.5 | 19 | 81 | — |
| 2. 15 | — | 82 | 80 | 83 | 103.7 | 33 | 67 | — |
| 3. 22.5 | — | 86 | 85 | 86 | 100 | 55 | 45 | — |
| 4. 30 | — | 89 | 87 | 88 | 93.7 | 58 | 42 | — |
| 5. 37.5 | — | 89 | 88 | 87 | 135 | 76 | 24 | — |
| 6. — | 4.5 | 84 | 79 | 77 | 111.8 | 57 | 43 | — |
| 7. — | 9.0 | 82 | 81 | 77 | 110.8 | 55 | 45 | — |
| 8. — | 13.5 | 90 | 87 | 87 | 171.9 | 69 | 31 | — |
| 9. — | 18.0 | 94 | 94 | 94 | 166.5 | 83 | 27 | — |
| Combination | | | | | | | | |
| 10. 7.5 | 4.5 | 91 | 91 | 91 | 139.3 | 97 | 3 | — |
| 11. 7.5 | 9.0 | 92 | 94 | 93 | 149.9 | 98 | 2 | — |
| 12. 7.5 | 13.5 | 96 | 95 | 96 | 133.6 | 100 | — | — |
| 13. 15.0 | 4.5 | 92 | 93 | 93 | 138.4 | 97 | 3 | — |
| 14. 22.5 | 4.5 | 92 | 93 | 93 | 112.4 | 95 | 5 | — |
| 15. 30.0 | 4.5 | 95 | 96 | 94 | 112.9 | 96 | 4 | — |

We claim:

1. A composition for combating pests of the order of Homoptera, Lepidoptera or Acarina which composition comprises abamectin in combination with a synergistically effective amount of endosulfan, heptenophos, or hexythiazox, wherein the compounds are present at a proportion of from 1 part of abamectin to 32 parts of endosulfan, 1 part of abamectin to 32 parts of heptenophos, or 1 part of abamectin to 2 to 4 parts of hexythiazox.

* * * * *